United States Patent [19]

Deneke et al.

[11] 4,271,265

[45] Jun. 2, 1981

[54] METHOD AND REAGENT FOR THE DETERMINATION OF GLUTAMATE-OXALACETATE TRANSAMINASE AND GLUTAMATE-PYRUVATE TRANSAMINASE

[75] Inventors: Ulfert Deneke, Peissenberg; Peter Stahl, Bernried; Walter Schneider, Weilheim, all of Fed. Rep. of Germany

[73] Assignee: Boehringer Mannheim GmbH, Mannheim-Waldhof, Fed. Rep. of Germany

[21] Appl. No.: 59,368

[22] Filed: Jul. 20, 1979

[30] Foreign Application Priority Data

Aug. 8, 1978 [DE] Fed. Rep. of Germany ....... 2834706

[51] Int. Cl.³ ............................ C12Q 1/32; C12Q 1/52
[52] U.S. Cl. ........................................ 435/16; 435/26; 435/805
[58] Field of Search ................... 23/230 B; 252/408 R; 435/4, 16, 26, 805

[56] References Cited

U.S. PATENT DOCUMENTS

| | | | |
|---|---|---|---|
| 3,069,330 | 12/1962 | Babson | 435/16 |
| 3,819,488 | 6/1974 | Rush et al. | 435/26 |
| 3,875,014 | 4/1975 | Forgione | 435/16 |
| 3,899,397 | 8/1975 | Morin et al. | 435/16 |
| 4,017,365 | 4/1977 | Nakayama et al. | 435/16 |
| 4,024,021 | 5/1977 | Stavropoulos et al. | 435/16 |
| 4,086,142 | 4/1978 | Huang et al. | 435/16 |

OTHER PUBLICATIONS

Henley et al., *J. Lab. Clin. Med.* 46, 1955, pp. 785–789.
Karmen, *J. Clin. Invest.*, 34, 1955, pp. 131–133.
Reitmann et al., *Am. J. Clin. Path.*, 28, 1957, pp. 56–63.
Babson, *Clin. Chem.*, 6, 1960, p. 394.
Matsuzawa et al., *Anal. Biochem.*, 17, 1966, pp. 143–153.
Jakoby et al., "Aldehyde Oxidation," *J. Biol. Chem.* 234, 1958, pp. 937–940.
*The Condensed Chemical Dictionary*, 8th Ed. Von Nostrand Reinhold Company, 1971.
Scott et al., "Soluble γAminobutyric-Glutamic Transaminase from Pseudomonas Fluorescens," *J. Biol. Chem.*, 234, 1958, pp. 932–936.
Lippi et al. *Clin. Chim. Acta*, 28, 1970, pp. 431–437.
Domecq et al. *Biochem. Clinica*, 2, 1971, pp. 25–36, 102–111.

*Primary Examiner*—Peter A. Hruskoci
*Attorney, Agent, or Firm*—Sprung, Felfe, Horn, Lynch & Kramer

[57] ABSTRACT

In a method for the determination of glutamate-oxalacetate transaminase or glutamate-pyruvate transaminase by the reaction of oxalacetate or pyruvate with glutamate, with formation of α-ketoglutarate in a buffered solution, the α-ketoglutarate formed is reacted with γ-aminobutyrate in the presence of γ-aminobutyrate transaminase with formation of succinate semialdehyde, NADP is reduced with the latter in the presence of succinate semialdehyde dehydrogenase to give NADPH, and the latter is measured either directly or after conversion with a tetrazolium salt and an electron carrier such as diaphorase, phenantroline methosulphate or phenazine methosulphate to a formazane dye.

A reagent suited for use with this method contains γ-aminobutyrate transaminase, succinate semialdehyde dehydrogenase, γ-aminobutyrate, glutamate and buffer, as well as either oxalacetate or pyruvate, and optionally a tetrazolium salt, an electron carrier and a surface-active agent.

13 Claims, No Drawings

METHOD AND REAGENT FOR THE DETERMINATION OF GLUTAMATE-OXALACETATE TRANSAMINASE AND GLUTAMATE-PYRUVATE TRANSAMINASE

The present invention is concerned with a method for the determination of the activity of the enzymes glutamate-oxalacetate transaminase (GOT) and glutamate-pyruvate transaminase (GPT), as well with a reagent for carrying out this method. The method can be used for the determination of these enzymes in biological fluids, such as serum, urine or in other materials.

The great diagnostic importance of the determination of these two transaminases in plasma, serum, tissues and other biological material has been known for a long time. In the case of diagnoses and differential diagnoses of, for example, liver, heart and muscular diseases, these determinations have been used since 1955 and even today remain unchallenged (see, for example, H. U. Bergmeyer, Methoden der enzymatischen Analyse, 3rd edition, 1974. Verlag Chemie, Weinheim, Volume I, pages 6 to 74). Therefore, various processes for the determination of GOT and GPT have been described which, however, all suffer from certain disadvantages.

The above-mentioned transaminases catalyse the following reactions:

(a) GPT

  (1)

(b) GOT

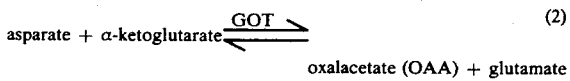  (2)

Several methods are already known for the determination of these enzymes. Thus, K. S. Henley and H. M. Pollard (J. Lab. Clin. Med., 46, 785–789/1955) have described the following method for the determination of GPT activity: reaction (1) is carried out with alanine and α-ketoglutarate (α-KG) and the formation of the pyruvate is measured as follows:

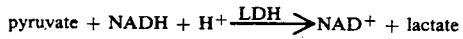  (3)

LDH=lactate dehydrogenase

The decrease of the absorption of NADH per minute, measured in UV light at 365 nm, is the measurement signal.

An analogous test using GOT has been described by A. Karmen (J. Clin. Invest., 34, 131–133/1955): the oxalacetate (OAA) formed according to equation (2) is hereby measured as follows:

  (4)

MDH=malate dehydrogenase

The decrease of the absorption of NADH per minute, measured at 365 nm in UV light, is the measurement signal.

Another procedure, which is said to be suitable not only for the detection of GPT but also of GOT, has been described by S. Reitmann and S. Fraenkel (Am. J. Clin. Path., 28, 56–63/1957). The pyruvate formed by GPT according to equation (1) or the OAA formed by GOT according to equation (2) is hereby reacted, simultaneously with the α-ketoglutarate present in the residue, with dinitrophenylhydrazine to give the corresponding coloured hydrazones which, after alkalisation, because of their differing absorption between 500 and 550 nm, can be jointly determined. The calculation is complicated but possible because the hydrazone of α-ketoglutarate, on the one hand, and the hydrazones of pyruvate and OAA, on the other hand, display differing extinctions in the measurement range.

However, it is also possible to couple the oxalacetate formed according to equation (2) with a diazonium salt to give a dye which can then be photometrically evaluated, such a procedure having been described by A. L. Babson (Clin. Chem., 6, 394/1960) for measuring the GOT activity.

For the measurement of the GPT activity, T. Matsuzawa and N. Katunuma (Anal. Biochem., 17, 143–153/1966) used the formation of α-KG according to equation (1). They converted the α-KG, by the addition of aspartate and crystalline GOT, according to equation (2), into OAA and then measured the formation thereof with the diazonium coupling method according to A. C. Babson. The amount of azo dyestuff formed can be measured in visible light and is a measure for the GPT or GOT activity in the sample.

U. Lippi and G. Guidi (Clin. Chim. Acta, 28, 431–437/1970) measured the GPT and GOT with the help of the glutamate liberated in equations (1) and (2) by subsequently adding the following two indicator reactions:

  (5)

  (6)

GlDH=glutamate dehydrogenase; PMS=phenazine methosulphate; INT=2-(p-iodophenyl)-3-(p-nitrophenyl)-5-phenyl-tetrazolium chloride.

For the determination of GOT, R. B. Domecq, M. Carta and E. F. de Armony (Biochem. Clinica, 2, 25–36/1971) combined the reaction sequence of equations (2) and (4) with equation (6), the decrease of the amount of NADH, measured as the formazane dye, in the particular test thereby becoming the measurement value. It can be monitored in visible light and is also a measure for the GOT activity in the sample. These authors have also described an analogous test for GPT (Biochim. Clinica, 2, 102–111/1971).

All the above-described test processes for the determination of the activities of GPT and GOT suffer from various grave deficiencies which make their use expensive or difficult. Thus, the procedures according to Henley and Pollard or according to A. Karmen admittedly permit the measurement of the change of extinction per minute of NADH, which is advantageous, but a UV test must be used. As is known to those skilled in the art, optical measurement devices for the measurement in UV light are, however, especially complex and, therefore, more expensive as measurement devices than measurement devices capable of measuring absorption changes in visible light. A further serious deficiency is that a decrease of the NADH extinction must be measured. In such a test, for measurement-technical reasons, only a limited initial concentration of NADH can be present. This has the result that the indicator enzymes LDH or MDH here used are not saturated with their substrate NADH and, consequently, cannot achieve a maximum reaction rate. This must be compensated for by an increased use of enzyme which is not only uneconomical but also includes the danger that other disturbing enzyme activities are introduced into the test system in comparatively large amounts. A further disadvantage of the low NADH concentration follows from the fact that not only in automatic analysers but also in the case of a manual test, a certain time elapses between the addition of the sample and the commencement of the measurement. If, now, a marked activity of the GPT or GOT is present in the sample, then a large part of the NADH will already be used up before commencement of the measurement. For this reason, particularly in the case of considerably increased GPT and GOT values, which provides indications of a pathological condition in the body, the measurement erroneously indicates too low an activity or no activity at all. This is a severe deficiency of these determinations.

In the case of the methods according to Reitman and Fraenkel, the hydrazones formed are determined in visible light. This enables the use of simpler and thus more favourably priced photometric devices. However, these methods suffer from other serious deficiencies. They are very insensitive and consequently require the very long incubation period of one hour. Only then has sufficient pyruvate or oxalacetate formed to enable the hydrazone formation to be initiated and this requires a further incubation period. Furthermore, the α-KG necessary in the test batch also reacts to give a coloured hydrazone. Thus, for the evaluation of this test, there are extremely complicated relationships since, at the same time, the decrease of α-KG hydrazone and the increase of pyruvate or OAA hydrazone must be taken into account. Those skilled in the art have long known that the use of these methods involves errors of up to 20 to 30%.

In principle, similar problems arise in the case of the methods according to Babson or according to Matsuzawa and Katunuma. Admittedly, it is here possible to measure in the visible light and, because α-KG does not interfere with the diazonium salt, the evaluation is substantially simpler; however, here, too, OAA or pyruvate must first be produced by a comparatively long incubation. Subsequently, the colour formation must be carried out in a further incubation stage. According to the method of Matsuzawa and Katunuma, the resultant azo dyestuff must still be stabilized by hydrochloric acid, which is unpleasant to handle. Furthermore, it is known to those skilled in the art that many keto compounds of similar structure coupled with diazonium salts to give dyes which interfere with the determination because they simulate too high values. Consequently, these errors must first be eliminated by means of a blank. Thus, for example, serum always contains varying amounts of acetoacetic acid which simulate the oxalacetate which is first to be formed in the GPT or GOT reaction.

The methods according to Lippi and Guidi also measure in visible region. They only require one incubation stage which, however, being a period of 45 minutes, is very long. The reaction must also then be stopped with the toxic and hazardous hydrochloric acid. It is a further disadvantage that relatively large amounts of glutamic acid are present in serum. According to equation (5), in both tests it simulates GOT or GPT. Therefore, here, too, a blank is necessary.

The procedure according to Domecq et al. also requires two incubation stages. Since it finally measures the decrease of NADH according to the methods of Henley and Pollard or of Karmen, the same disadvantages here apply as there indicated but are more marked because, for measurement technical reasons, even less NADH must be used. Although measurement in visible light is advantageous, here, too, the complete consumption of NADH by too high activities in the sample solution cannot be overlooked. However, in all, as is readily apparent to those skilled in the art, the procedure is very laborious and susceptible to disturbance because very high demands are placed upon the precise dosing of NADH in each measurement value.

Therefore, it is an object of the present invention to provide a method for the determination of the activities of the two above-mentioned transaminases which does not display the disadvantages of the known processes. In particular, it is an object of the present invention to provide a method which only requires a short measurement time and only one incubation, which measures the change of absorption per minute, leads to an increase in absorption and not to a decrease in absorption and also permits measurement in visible light, thereby enabling simpler photometric devices to be used.

Thus, according to the present invention, there is provided a method for the determination of glutamate-oxalacetate transaminase or of glutamate-pyruvate transaminase by the reaction of oxalacetate or pyruvate with glutamate with the formation of α-ketoglutarate in buffered solution, wherein α-ketoglutarate formed is reacted with γ-aminobutyrate in the presence of γ-aminobutyrate transaminase with the formation of succinate semi-aldehyde, NADP is reduced with the latter in the presence of succinate-semialdehyde dehydrogenase to give NADPH and this is either measured directly or is converted with a tetrazolium salt and an electron carrier into a formazane dye which is then measured.

The principle of the method according to the present invention consists in the combination of the reactions of equation (1) or (2) with those of the following equations (7) and (8):

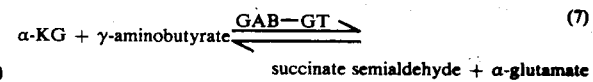

(7)

GAB-GT = γ-aminobutyrate transaminase

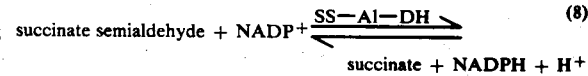

(8)

SS-Al-DH = succinate-semialdehyde dehydrogenase

These equations are known (see J. Biol. Chem., 234, 932–940/1958). Surprisingly, it has now been found, and this is what the present invention is based on, that it is possible to couple the reactions of equations (7) and (8) with the reactions of equations (1) and (2), via the formation of α-KG. In this way, the increase of absorption per unit time due to the NADPH formed becomes a measure of the activity of GPT or GOT, respectively. Hitherto, such a coupling was not deemed to be possible which follows alone from the fact that, for more than 20 years, a search has been made for a satisfactory procedure for the determination of GOT and GPT and also that the reactions have been known for such a long time.

According to an especially advantageous embodiment of this method a subsequent reaction is carried out in which, with a tetrazolium salt in the presence of an electron carrier, re-oxidation of NADPH takes place, with the simultaneous formation of a formazane dye which can easily be measured in visible light. In a preferred embodiment, this corresponds to the following equation:

$$\text{NADPH} + \text{MTT} + \text{H}^+ \xrightarrow{\text{diaphorase}} \text{formazane} + \text{NADP}^+ \quad (9)$$

MTT=3-(4,5-dimethylthiazol-2-yl)-2,5-diphenyl-tetrazolium bromide.

The diaphorase used in equation (9) as the electron carrier is preferred. However, other electron carriers known to those skilled in the art can also be used. Thus, for example, phenazine methosulphate (PMS) and phenanthroline methosulphate have proved to be very suitable. This embodiment is also well suited for use on test strips.

The method according to the present invention is, in general, carried out at a pH value of from 7 to 9.5. In the case of higher and lower pH values, there is a considerable slowing down of the reaction, with a corresponding lengthening of the time needed per test. The best results are achieved at pH values of from about 8 to 8.6.

Preferred buffer concentrations are from 5 mMol/l. to 0.5 mol/l., corresponding to about 0.05 to 6% of buffer salt in the test. The buffer is preferably employed in a concentration of from about 10 to about 100 mMol/l.

In general, the nature of the buffer used is not critical, provided that the buffer action is exerted in the above-mentioned range. Thus, for example, comparably good results have been achieved with phosphate buffer, triethanolamine buffer, glycine buffer, pyrophosphate buffer, tris buffer and imidazole buffer. For measurement technical and handling reasons, the two last-mentioned buffers are preferred. The other reagents and enzymes used in the method according to the present invention can be used in a wide concentration range without the result of the measurements being changed. In no case it is necessary to maintain critically narrow limits for one of the reagents.

The tetrazolium salt preferably used is the above-mentioned MTT although other tetrazolium salts can also be employed. In particular, good results have also been achieved with the use of nitro blue tetrazolium chloride (NBT) and 2-(p-iodophenyl)-3-(p-nitrophenyl)-5-phenyltetrazolium chloride (INT). The choice of the tetrazolium salt used depends upon the solubility of the formazane dye formed. Thus, if the latter has a low solubility then, in the case of high GOT or GPT activities, precipitation of the dye can occur, which can give rise to measurement difficulties. For this reason, when carrying out the procedure according to the present invention, with measurement of a formazane dye, it is preferable to add a surface-active agent, which improves the solubility of the dye. Examples of surface-active agents which can be used include desoxycholic acid, saponin alkylaryl-polyethylene glycol esters and ethers, sorbitan esters, such as sorbimacrogol oleate, polyethylene glycol lauryl ester and the like. In general, the concentration of the surface-active agent in the test is from 0.3 to 3%.

The present invention also provides a reagent for the determination of GOT and GPT, which comprises γ-aminobutyrate transaminase (GAB-GT), succinate-semialdehyde dehydrogenase (SS-Al-DH), γ-aminobutyrate, glutamate and buffer, as well as either oxalacetate or pyruvate and optionally a tetrazolium salt, an electron carrier and a surface-active agent.

The γ-aminobutyrate, glutamate, oxalacetate and pyruvate are salts of the acids in question with cations which do not impair the enzymatic reaction. In general, alkali metal, ammonium and amino salts are preferred but magnesium salts and the like can, however, also be used.

A preferred reagent according to the present invention comprises:

0.5 to 20 U/ml. SS-Al-DH
0.5 to 20 U/ml. GAB-GT
0.1 to 50 mMol/l. pyruvate or oxalacetate
0.02 to 0.5 mol/l. glutamate
10 to 300 mMol/l. γ-aminobutyrate
0.2 to 10 mMol/l. NADP and
10 to 100 mMol/l. buffer, in each case referred to the concentration in the test. The reagent can be present in dry form or in the form of a solution. All the components can be present mixed together or separate.

Such a reagent preferably additionally comprises:

0.02 to 1 U/ml. diaphorase,
0.02 to 0.5 mMol/l. MTT, INT or NBT and
0.3 to 3% of a surface-active agent.

The diaphorase can also be replaced by a non-enzymatically-acting electron carrier. This reagent is also especially suitable for the impregnation of or for incorporation into carrier materials for the production of test strips.

The determination according to the method of the present invention proceeds quickly. An incubation period of from 1 to 5 minutes and preferably of about 2 minutes suffices completely. After the start of the reaction by the addition of the sample solution to be investigated, the measurement is finished after a few minutes. As a rule, the extinction difference is measured per minute. For this purpose, a few measurement values suffice, which are taken within 1 or 2 minutes. For the purpose of simplicity, two to four measurement values are taken at one minute intervals.

The method according to the present invention is characterised by high accuracy, small time requirement, low susceptibility to disturbance and the ability to be carried out with simple photometric devices. Since the measurement of the absorption change takes place per minute, the measurement time is short. Furthermore, only a single incubation is necessary. A substantial advantage lies in the fact that the absorption change represents an absorption increase so that the measurement parameter need not be employed in limited amounts and as deceptively high values of GPT or GOT activity are obtained, as is the case with procedures in which an absorption decrease takes place.

The following abbreviations are used in the Examples which follow:
GPT: glutamate-pyruvate transaminase
GAB-GT: γ-aminobutyrate-α-ketoglutarate transaminase
SS-Al-DH: succinate-semialdehyde dehydrogenase
GOT: glutamate-oxalacetate transaminase NADP: nicotinamide-adenine-dinucleotide phosphate
NADPH: nicotinamide-adenine-dinucleotide phosphate, reduced
MTT: 3-(4,5-dimethylthiazol-2-yl)-2,5-diphenyltetrazolium bromide
Tris: tris-(hydroxymethyl)-aminomethane
Triton ® X100: alkylaryl-polyethylene glycol ether.

The following Examples are given for the purpose of illustrating the present invention:

EXAMPLE 1

Detection of GPT with NADPH formation as the measurement signal

Temperature: 25° C.; wavelength 365 nm; test volume 3 ml.; 1 cm.

| starting solution | amount | concentration in the test |
| --- | --- | --- |
| Tris HCl, pH 3.3, 50 mMol/l. (= 0.6055%) | 1.5 ml. | 25 mMol/l. (= 0.30275%) |
| NADP, 27 mMol/l.(= 2%) | 0.1 ml. | 0.9 mMol/l. (= 0.067%) |
| $\gamma$-aminobutyrate, 0.9 mMol/l., pH 8.3 (= 9%) | 0.2 ml. | 60 mMol/l. (= 0.06%) |
| glutamate, 0.6 mol/l., pH 8.3 (= 8.8%) | 0.5 ml. | 0.1 Mol/l. (= 1.47%) |
| sodium pyruvate, 0.55 mol/l., (= 6%) | 0.03 ml. | 5.4 mMol/l. (= 0.06%) |
| GAB-GT, 86 U/ml. (= 11% protein) | 0.05 ml. | 1.43 U/ml. (= 0.183%) |
| water | 0.02 ml. | | mix, start with

| serum (GPT-containing) | 0.5 ml. |
| --- | --- | mix, incubate for 2 minutes, read off $E_1$, after precisely 1, 2, 3 and 4 minutes, read off $E_2$, $E_3$, $E_4$ and $E_5$. From this calculate the $\Delta E$/min. The GPT activity in the sample is calculated from $$U/ml. = (E \cdot V)/(\epsilon \cdot v) = \Delta E \cdot 1.714$$

EXAMPLE 2

GPT determination with formazane formation as the measurement signal

Temperature 25° C.; wavelength 578 nm; test volume 3 ml.; 1 cm. cuvette.
Into the cuvette transfer by pipette:

| starting solution | amount | concentration in the test |
| --- | --- | --- |
| Tris HCl, pH 3.3 50 mMol/l. (= 0.6055%), containing 2% "Triton" X100 | 1.5 ml. | "Triton" X100 (= 1%) Tris 25 mMol/l. (= 0.30275%) |
| NADP, 27 mMol/l. (= 2%) | 0.1 ml. | 0.9 mMol/l. (= 0.067%) |
| $\gamma$-aminobutyrate, 0.9 mol/l. (= 9%) | 0.2 ml. | 60 mMol/l. (= 0.06%) |
| glutamate, 0.6 mol/l. (= 8.8%) | 0.5 ml. | 0.1 mol/l. (= 1.47%) |
| sodium pyruvate, 0.55 mol/l. (= 6%) | 0.03 ml. | 5.4 mMol/l. (= 0.06%) |
| MTT, 1.5 mMol/l. (= 0.0621%) | 0.2 ml. | 0.1 mMol/l. (= 0.00414%) |
| GAB—GT, 86 U/ml. (= 11% protein) | 0.05 ml. | 1.43 U/ml. (= 0.183%) |
| SS—Al—DH, 133 U/ml. | 0.05 ml. | 2.2 U/ml. (= 0.183%) |
| (= 11% protein) diaphorase, 23 U/ml. (= 0.5% protein) | 0.01 ml. | 0.077 U/ml. (= 0.0017%) |
| water | 0.26 ml. | | mix, start with

| serum (GPT-containing) | 0.1 ml. |
| --- | --- | mix, incubate for 2 minutes, read off $E_1$, after precisely 1, 2, 3 and 4 minutes, read off $E_2$, $E_3$, $E_4$ and $E_5$ and calculate $\Delta E$/min. therefrom. The GPT activity in the sample is calculated as follows:

$$U/ml. = (E \cdot V)/(\epsilon \cdot v) = \Delta E \cdot 1.796$$

EXAMPLE 3

GOT determination with NADPH formation as the measurement signal

Measurement temperature 25° C.; measurement wavelength 365 nm; test volume 3 ml.; 1 cm cuvette. Into the cuvette transfer by pipette:

| starting solution | amount | concentration in the test |
| --- | --- | --- |
| imidazole HCl, pH 7.6 100 mMol/l. (= 6.808%) | 1.5 ml. | 50 mMol/l. (= 3.404%) |
| NADP, 27 mMol/l. (= 2%) | 0.1 ml. | 0.9 mMol/l. (= 0.067%) |
| $\gamma$-aminobutyrate, 0.9 mol/l. pH 8.3 (= 9%) | 0.3 ml. | 90 mMol/l. (= 0.9%) |
| glutamate, 0.6 mMol/l., pH 8.3 (= 8.8%) | 0.3 ml. | 60 mMol/l. (= 0.88%) |
| oxalacetate, 20.8 mMol/l. (= 0.275%) | 0.1 ml. | 0.65 mMol/l. (= 0.00917%) |
| GAB-GT, 86 U/ml. (= 11% protein) | 0.05 ml. | 1.43 U/ml. (= 0.183%) |
| SS-Al-DH, 133 U/ml. (= 11% protein) | 0.05 ml. | 2.22 U/ml. (= 0.183%) |
| water | 0.1 ml. | | mix, start with

| serum (GOT-containing) | 0.5 ml. |
| --- | --- | mix, incubate for 2 minutes, read off $E_1$, after precisely 1, 2, 3 and 4 minutes read off $E_2$, $E_3$, $E_4$ and $E_5$ and calculate $\Delta E$/min. therefrom. The GOT activity in the sample is calculated from:

$$U/ml. = (\Delta E \cdot V)/(\epsilon \cdot v) = \Delta E \cdot 1.717$$

EXAMPLE 4

Detection of GOT with formazane formation as the measurement signal

Temperature 25° C.; measurement wavelength 573 nm; test volume 3 ml.; 1 cm. cuvette.
Into the cuvette transfer by pipette:

| starting solution | amount | concentration in the test |
|---|---|---|
| imidazole HCl, pH 7.6 100 mMol/l. (= 6.808%) + 3% "Triton" X100 | 1.5 ml. | imidazole 50 mMol/l. (= 0.30275%) "Triton" X100 (= 1.5%) |
| NADP, 27 mMol/l. (= 2%) | 0.1 ml. | 0.9 mMol/l. (= 0.067%) |
| γ-aminobutyrate, 0.9 mMol/l., pH 8.3 (= 9%) | 0.3 ml. | 90 mMol/l. (= 0.9%) |
| glutamate, 0.5 mol/l., pH 8.3 (= 8.8%) | 0.3 ml. | 60 mMol/l. (= 0.88%) |
| oxalacetate, 20.8 mMol/l. (= 0.275%) | 0.1 ml. | 0.65 mMol/l. (= 0.00917%) |
| MTT, 1.5 mMol/l. (= 0.0621%) | 0.2 ml. | 0.1 mMol/l. (= 0.00414%) |
| GAB—GT, 86 U/ml. (= 11% protein) | 0.05 ml. | 1.43 U/ml. (= 0.183%) |
| SS—Al—DH, 133 U/ml. (= 11% protein) | 0.05 ml. | 2.22 U/ml. (= 0.183%) |
| diaphorase, 23 U/ml. (= 0.5% protein) | 0.01 ml. | 0.077 U/ml. (= 0.0017%) |
| water | 0.24 ml. | | mix, start with

| serum (GOT-containing) | 0.05 ml. |
|---|---| mix, incubate for 2 minutes, read off $E_1$ and after precisely 1, 2, 3 and 4 minutes, read off $E_2$, $E_3$, $E_4$ and $E_5$. The GOT activity of the sample is calculated as follows:

$$U/ml. = (\Delta E \cdot V)/(\epsilon \cdot v) = \Delta E \cdot 3.593$$

EXAMPLE 5

Detection of GPT on test strips

An appropriate paper is impregnated with a solution which contains all the reagents of Example 2, then carefully dried, fixed on to an appropriate carrier material, sealed in and cut up into strips. After dipping into serum, a red-blue colour results, the intensity of which is proportional to the GPT activity in the sample. Evaluation can take place by comparison with an appropriate standard colour scale. Evaluation is also possible with a reflection photometer.

EXAMPLE 6

Detection of GOT on test strips

An appropriate paper is impregnated with a reagent solution prepared according to Example 4, then carefully dried, fixed on to an appropriate carrier material, optionally sealed in and cut up into strips. After dipping into serum, a red-blue colour results, the intensity of which is proportional to the GOT activity in the sample. Evaluation can take place by comparison with an appropriate standard colour scale. Evaluation with a reflection photometer is also possible.

We claim:

1. In a method for the determination of glutamate-oxalacetate transaminase or of glutamate-pyruvate transaminase by the reaction of oxalacetate or pyruvate with glutamate with the formation of α-Ketoglutarate in buffered solution, the improvement comprising reacting the α-Ketoglutarate formed with γ-aminobutyrate in the presence of γ-aminobuyrate transaminase to form succinate semialdehyde, reducing NADP with said succinate semialdehyde in the presence of succinate semialdehyde dehydrogenase to form NADPH and measuring the NADPH as a measure of the glutamate transaminase component initially present.

2. Improvement as claimed in claim 1 wherein said NADPH is converted with a tetrazolium salt and an electron carrier into a formazane dye which is measured as a measure of the initial glutamate transaminase component.

3. Improvement as claimed in claim 2 wherein said tetrazolium salt is selected from 3-(4,5-dimethylthiazol-2-yl)-2,5-diphenyltetrazolium bromide, nitro blue tetrazolium chloride and 2-(p-iodophenyl)-3-(p-nitrophenyl)-5-phenyl-tetrazolium chloride.

4. Improvement as claimed in claim 1 wherein the reactions are carried out at a pH value of from 7 to 9.5.

5. Improvement as claimed in claim 1 wherein a buffer concentration of from 0.05 to 6% is used.

6. Improvement as claimed in claim 2 wherein said electron carrier is selected from diaphorase, phenanthroline methosulphate or phenazine methosulphate.

7. Reagent for the determination of glutamate-oxalacetate transaminase or of glutamate-pyruvate transaminase, comprising 0.5 to 20 U/ml γ-aminobutyrate transaminase, 0.5 to 20 U/ml succinate-semialdehyde dehydrogenase, 10 to 300 mMol/l γ-aminobutyrate, 0.2 to 10 mMol/l. NADP 0.02 to 0.5 mol/l glutamate and 10 to 100 mMol/l buffer, as well as 0.5 to 50 mMol/l of either oxalacetate or pyruvate.

8. Reagent according to claim 7 further comprising a tetrazolium salt, an electron carrier and a surface-active agent.

9. Reagent according to claim 8, comprising diaphorase, phenanthroline methosulphate or phenazine methosulphate as electron carrier.

10. Reagent according to claim 8, comprising 3-(4,5-dimethylthiazol-2-yl)-2,5-diphenyltetrazolium bromide, nitro blue tetrazolium chloride or 2-(p-iodophenyl)-3-(p-nitrophenyl)-5-phenyl-tetrazolium chloride as the tetrazolium salt.

11. Reagent according to claim 7, which additionally comprises:
   0.02 to 1 U/ml. diaphorase,
   0.02 to 0.5 mMol/l. 3-(4,50dimethylthiazol-20yl)-2,5-diphenyl-tetrazolium bromide and
   0.3 to 3% of a surface-active agent,
referred to the concentration in the test.

12. Reagent according to any of claim 7, 9, 10 or 11, comprising tris buffer or imidazole buffer.

13. In a method for the determination of glutamate-oxalacetate transaminase or of glutamate-pyruvate transaminase by the reaction of oxalacetate or pyruvate with glutamate with the formation of α-ketoglutarate in buffered solution, the improvement comprising reacting the α-ketoglutarate with the reagent of claim 6.

* * * * *